United States Patent [19]

Moll et al.

[11] 4,425,918
[45] Jan. 17, 1984

[54] MEMBRANE RETAINER ARRANGEMENT FOR PHYSIOLOGICAL SENSING UNITS

[75] Inventors: Hermann Moll; Helmut J. Leist; Karl-Heinz Pomorin; Georg J. Ullrich, all of Freiburg im Breisgau, Fed. Rep. of Germany

[73] Assignee: Hellige GmbH, Freiburg im Breisgau, Fed. Rep. of Germany

[21] Appl. No.: 307,722

[22] Filed: Oct. 2, 1981

[30] Foreign Application Priority Data

Oct. 28, 1980 [DE] Fed. Rep. of Germany ....... 3040544

[51] Int. Cl.³ .............................................. A61B 5/00
[52] U.S. Cl. ..................................... 128/635; 204/415
[58] Field of Search ............................. 128/635, 632; 204/195 B, 195 P, 415, 403

[56] References Cited

U.S. PATENT DOCUMENTS

| | | | |
|---|---|---|---|
| 4,005,700 | 2/1977 | Parker | 204/195 P X |
| 4,175,028 | 11/1979 | Payton | 204/195 P X |
| 4,273,134 | 6/1981 | Ricciardelli | 128/635 |
| 4,303,076 | 12/1981 | Danek | 128/635 |

FOREIGN PATENT DOCUMENTS

8460 3/1980 European Pat. Off. ............ 128/635

*Primary Examiner*—Lee S. Cohen
*Attorney, Agent, or Firm*—Robert A. Seldon

[57] ABSTRACT

Disclosed herein is a retainer arrangement for applying a membrane to a physiological sensing unit for the transcutaneous determination of the magnitude of physiological quantities, particularly for measuring the partial pressure of gases in blood or the like. The arrangement constitutes a preassembly of a membrane, with a clamping ring accommodating the membrane and having an annular recess receiving the rim of the membrane. The clamping ring has a lip in the form of an inwardly protruding annular edge for removably securing the clamping ring together with the membrane to the sensing unit by virtue of the lip resiliently snapping into a peripheral groove of the sensing unit, the lip defining the periphery of the annular recess. In accordance with the invention, an auxiliary retainer element, is provided for temporarily and removably assembling the membrane with the clamping ring prior to assembly with the sensing unit. The auxiliary retainer element includes a retainer ring fitted loosely into the annular recess of the clamping ring, to maintain the outer rim of the membrane within the annular recess.

13 Claims, 2 Drawing Figures

MEMBRANE RETAINER ARRANGEMENT FOR PHYSIOLOGICAL SENSING UNITS

FIELD OF THE INVENTION

The invention relates to physiological sensing units for the transcutaneous determination of the concentration of substances, particularly the partial pressure of gases, such as $O_2$ and $CO_2$, within blood and within body tissue, and it is particularly concerned with a retainer arrangement for the measuring surface members of such sensing unit.

DESCRIPTION OF THE PRIOR ART

Physiological sensing units for the transcutaneous determination of the partial pressure of gases within blood or within body tissue employ, for the purpose of performing the measuring step, one or several electrodes and a counterelectrode embedded within a measuring surface. Prior to the measuring step, a user of the device must polish the electrodes and the counterelectrode, whenever necessary. They must then be coated with an electrolyte and covered with a membrane. These preparatory steps must be repeated whenever the physiological sensing unit is intended to be used for performing a measuring step on a different individual or whenever the unit is to be used over extended periods of time, such as one week or longer, in connection with the same individual. In the course of clinical routine operation, it is important that these preparations can be attended to without excessive loss of time and still with high reliability.

In an earlier development of physiological sensing units of the type described above, a clamping ring is used for mounting the membrane to the measuring surface of the unit. The clamping ring is secured to the sensing unit by means of a threaded ring which surrounds the clamping ring. When preparing the sensing unit for use, the round membrane must firstly be aligned with the round measuring surface of the sensing unit in a concentric manner. Subsequently, the membrane must be secured in its working position by means of the clamping ring and, finally, the clamping ring must, in turn, be secured in its position by the threaded ring. Applying the membrane to the sensing unit therefore requires several sequential steps whose performance can lead to difficulties and loss of time, particularly when unskilled personnel is employed in a clinical routine environment.

Consequently, there exists a need for a possibility of securing the membrane to the measuring surface of a physiological sensing unit by simplified manipulations.

In the previously filed, copending application Ser. No. 276,184, filed June 22, 1981, now U.S. Pat. No. 4,359,054 assigned to the same assignee as this application, of which the present invention constitutes a further development, there are explained the difficulties which result in clinical routine when changing the membrane of a transcutaneous physiological, for example of a polarographic, sensing unit. The major difficulty is mainly that of properly centering the membrane, which usually is a thin transparent film about the size of a small coin and must be applied to the measuring surface of the sensing unit.

The above-mentioned copending application discloses a retainer arrangement for applying a membrane to a physiological sensing unit for the transcutaneous determination of the magnitude of physiological quantities, particularly for measuring the partial pressure of gases in blood or the like, wherein the retainer arrangement comprises a membrane, a clamping ring for removably assembling the membrane with the sensing unit, and means, including an auxiliary retainer element, for temporarily and removably securing the membrane to the clamping ring prior to assembly with the sensing unit. This earlier development starts out from the thought of providing preassemblies constituting spare parts, each in the form of a combination of a membrane for the sensing unit with a retainer ring for removably mounting the membrane to the sensing unit, with such preassemblies being adapted for use as the retainer arrangement for applying a membrane to a physiological sensing unit for the transcutaneous determination of the magnitude of physiological quantities, particularly for measuring the partial pressure of gases in blood or the like.

In accordance with the specific embodiment of the invention disclosed in the copending application, the membrane retainer arrangement is a preassembly of the membrane with the clamping ring, supplied as a spare part, and thus ready to be fitted, i.e. secured, to the measuring surface of the sensing unit. The membrane is secured to the clamping ring by means of a small plastic foam, self-adhesive disc inserted into the central space of the clamping ring, so that, when the clamping ring is pressed onto the sensing unit, the membrane is automatically centered on the measuring surface and stretched taut. The user of the sensing unit now no longer has to align the various parts (membrane, clamping ring, sensing unit) each with all others when performing the preparatory operations. It is simply necessary to place the clamping ring, with the membrane secured to it as a prefabricated spare part, on the prepared sensing unit and, after positioning, to remove the plastic foam disc which only loosely adheres to the clamping ring and the membrane.

Although this earlier proposed solution allows rapid, satisfactory changing of the measuring surface membrane even by personnel with little training, some disadvantages and shortcomings were found to exist in practice and in particular in the manufacture of the retaining device. For one thing, the membrane, which is permeable to the substance to be detected (e.g. $O_2$ or $CO_2$), is extremely susceptible to contamination. It is thus desirable, not only for reasons of hygiene but also to avoid inaccurate measurement results, that the membrane be kept perfectly clean. According to the proposal of the earlier filed, copending application, the foam disc inserted in the central space of the clamping ring is provided with a self-adhesive coating, whereby the membrane is secured to the clamping ring. The self-adhesive coatings known today, such as are used often in the medical field, are chemically inert, so that no undesirable reactions need be feared at the membrane surface facing toward the skin of the test subject. However, the permeability characteristics of the membrane must be expected to change under certain circumstances, due to long-term changes in the adhesive coating, and the possibility of occurrence of this adverse effect should be avoided.

Another aspect is the desirability of easy production of the retaining device. Insertion of an adhesive-coated plastic disc, with the membrane attached to it, into the central space of the clamping ring requires a relatively high expenditure in production.

The invention is therefore based on the need for improving the retaining device for the measuring surface membrane of a transcutaneous physiological sensing unit of the type contemplated in such a way that impairment of the characteristic properties of the membrane, in particular with regard to permeability to the substance to be detected by measurement (e.g. $O_2$ or $CO_2$), is reliably excluded. At the same time, the invention is intended to introduce a further simplification of the step of changing the membrane on the sensing unit and to provide a device which can be manufactured inexpensively.

SUMMARY OF THE INVENTION

In accordance with a broad aspect of the invention, there is provided a retainer arrangement for applying a membrane to a physiological sensing unit for the transcutaneous determination of the magnitude of physiological quantities, particularly for measuring the partial pressure of gases in blood or the like. The arrangement, which is of the nature of a preassembly, comprises a membrane, a clamping ring accommodating the membrane and having an annular recess receiving the rim of the membrane, the clamping ring having a lip in the form of an inwardly protruding annular edge for removably securing the clamping ring, together with the membrane, to the sensing unit by virtue of the lip resiliently snapping into a peripheral groove of the sensing unit, the lip defining the periphery of the annular recess, and means, including an auxiliary retainer element, for temporarily and removably assembling the membrane with the clamping ring prior to assembly with the sensing unit, wherein the auxiliary retainer element includes a retainer ring fitted loosely into the annular recess of the clamping ring, the retainer ring maintaining the outer rim of the membrane within the annular recess.

In accordance with a different aspect of the invention, the auxiliary retainer element for temporarily and removably assembling the membrane with the clamping ring prior to assembly with the sensing unit may include a film disc whose rim is removably fitted into the annular recess of the clamping ring.

In a particularly useful embodiment, the preassembly may include a removable self-adhesive backing film for temporarily supporting at least one clamping ring accommodating a membrane by adhesion to the lip of the clamping ring and to the central surface area which is surrounded by the lip. Advantageously, the backing film is a strip supporting a plurality of clamping rings, each accommodating one membrane, for ready use by removal from the backing strip and assembly with a physiological sensing unit.

Due to the retaining ring according to the invention, which retains the membrane loosely assembled with the clamping ring of the retaining device, the additional foam disc with self-adhesive coating of the earlier filed, copending application can be avoided, so that impairment of the permeability characteristics of the membrane no longer need be feared.

Thus, in an advantageous development of the invention, the membrane which covers the open central space of the clamping ring is covered by a protective film disc which is removed shortly before changing the membrane. A plurality of such clamping rings, each provided with a protective film disc, assembled with a membrane in the centered position and covered by the protective film, can be pressed against, and then supported by, a self-adhesive protective and retaining common band, i.e. backing strip, for easier handling and storage.

BRIEF DESCRIPTION OF THE DRAWINGS

The invention and advantageous details will become better understood from the following description of an exemplary embodiment illustrated in the drawing, in which.

In the figures of the drawing, mutually corresponding elements are identified by use of the same reference characters.

DETAILED DESCRIPTION OF A PREFERRED EMBODIMENT

Figure 1:
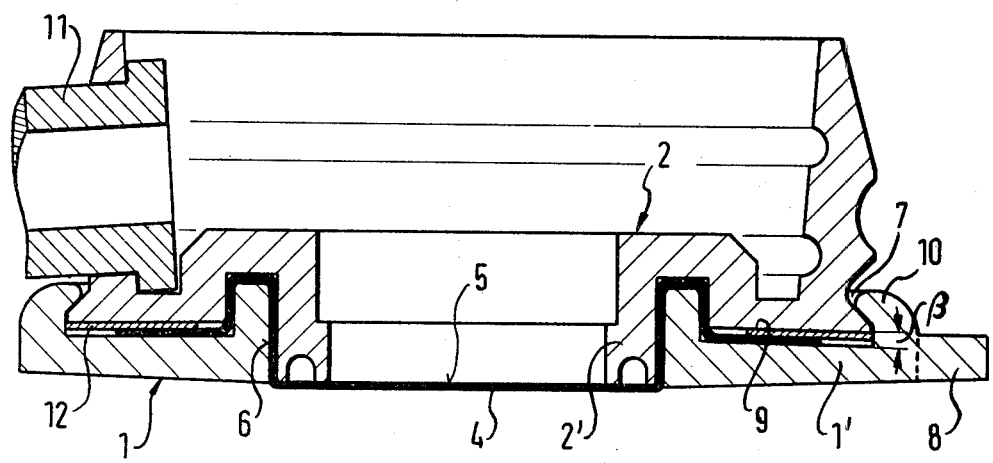
FIG. 1 is a sectional view through the housing of a physiological sensing unit having a clamping ring assembled therewith, together with a membrane and a retainer ring.

FIG. 1 shows a housing main body 2 of a physiological sensing unit with lateral signal delivery via a cable 11. The construction of the detector, i.e. the sensing element proper, is in accordance with conventional technology and therefore does not require any further explanation herein. The measuring surface 5 of the sensing unit, defined as the area within a downwardly projecting peripheral edge 2' of the housing main body 2, is covered by a circular membrane 4 of thin film material, for example of the plastic material polytetrafluoroethylene known under the trade name "Teflon", of polypropylene or polyethylene, and which appears essentially thicker in the diagrammatic view than corresponds to the actual proportions. The drawing illustrates the sensing unit in a view enlarged about ten times.

FIG. 1 shows the membrane 4 which covers the measuring surface 5 and which is kept stretched mainly at the mating surface 6 by the clamping ring 1. The clamping ring 1 itself is assembled with the housing 2 by means of a lip in the form of a retaining edge 10 which is slightly bent to protrude inwardly at its outer edge, as the lip engages a peripheral groove 7 in the lower outer surface area of the housing 2. The outer edge of the clamping ring 1 may be provided with a gripping handle or tab 8 by which the clamping ring 1 can easily be removed when a membrane change is necessary.

Figure 2:
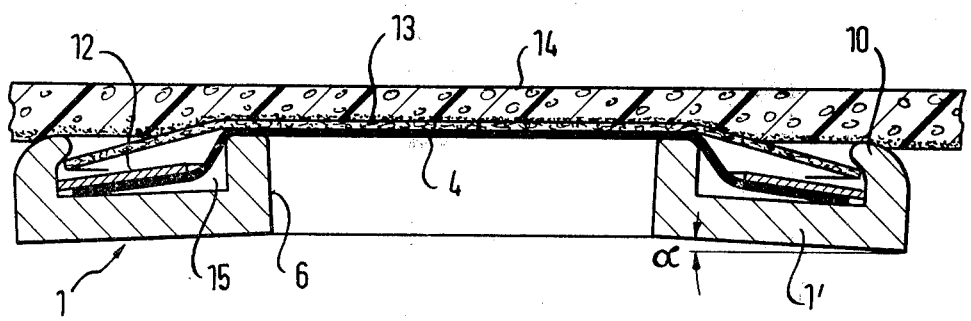
FIG. 2 is a sectional view through the preassembly of a clamping ring, thus constituting a spare part, prior to application of the membrane to the sensing unit.

FIG. 2 shows the clamping ring preassembly as an exchangeable spare part. As illustrated, the open central space of the clamping ring is covered on the top side by the membrane 4. The membrane 4 is loosely fitted into the annular recess 15 of the clamping ring, as shown, the lip deforming the periphery of the annular recess. The outer rim of the membrane 4 is maintained within the recess 15 of the clamping ring 1 by a retaining ring 12 which is inserted from the top into the annular recess 15. The recess is defined between the inwardly bent retaining edge forming lip 10 and the clamping wall surface of the clamping ring 1. The retaining ring 12 covers the peripheral outer rim of the membrane 4. Its outside diameter is dimensioned so that it fits under slight pressure below the retaining edge or lip 10 on the inside of the lip and retains the membrane 4 and holds it taut.

On its upper side, the membrane 4 is covered by a protective film disc 13 which is suitably a round disc of stiff paper with an outside diameter which is likewise slightly greater than the diameter of the clamping ring at the upper, inner periphery of the lip, i.e. retaining edge 10. The protective film disc 13 thus likewise engages beneath the lip 10, so that the delicate film material constituting the membrane 4 is protected on its upper side.

A protective retaining bond 14, conveniently referred to as a backing strip, serves to facilitate handling and storing several preassemblies of retaining rings provided with membranes. A self-adhesive coating upon band 14 into which, as FIG. 2 reveals, the clamping ring 1 with the protective film disc 13 can be lightly pressed may constitute a common support for a plurality of preassemblies, inasmuch as the self-adhesive coating of the protective retaining band 14 adheres firmly to the upper edge of the lip 10 and also to the outer surface of the protective film disc 13 with relatively slight adhesive action. In the view of FIG. 2, the gripping bar or tab 8 is not shown.

To change a membrane 4 on the physiological sensing unit, the procedure is as follows:

The clamping ring 1 with the membrane 4 loosely secured to it and already centered by the retaining ring 12, as shown in FIG. 2, is removed from the protective retaining band 14. In this step, the protective film disc 13 remains adhered to the protective retaining band 14. Then the clamping ring 1 with the membrane 4 is fitted over the mating surface 6, thereby to tautly pull the membrane 4 over the measuring surface 5, as the membrane is urged against the mating surface 6. The region of outer edge 1' of clamping ring 1 is pressed against the lower surface of the housing 2, so that the lip 10 engages, i.e. resiliently snaps into, the peripheral groove 7.

An additional gripping and clamping effect is achieved by the fact that the annular flange 1' of the clamping ring is slightly inclined (angle $\alpha$) from the inside to the outside in the unassembled state, as shown in FIG. 2, whereby, once the retaining edge or lip 10 engages the peripheral groove 7, a pressing stress results at the lower surface 9 of the housing 2. To still further improve, i.e. increase, the clamping action of the clamping ring at the conical mating surface 6, the bearing surface 9 of the clamping ring 1 of the housing 2 may be bevelled from the inside to the outside at an angle $\beta$ of 2° to 6°, preferably about 4°, as explained in the above-mentioned earlier application.

The clamping ring preassembly according to the invention, suitably constituting an exchangeable spare part, with the membrane 4 assembled with the clamping ring loosely maintained in the assembled position by the retaining ring 12, where it is protected by the protective film disc 13, can easily be manufactured under mass production conditions, without the risk of modifying the permeability of the membrane or in any other way reduce the usefulness of the membrane retainer arrangement.

What is claimed is:

1. A retainer arrangement for applying a membrane to a physiological sensing unit for the transcutaneous determination of the magnitude of physiological quantities, particularly for measuring the partial pressure of gases in blood or the like, comprising:
    a membrane;
    a clamping ring having a generally central opening and a peripheral annular recess receiving the rim of the membrane so that the membrane spans the opening;
    the clamping ring having a lip in the form of an inwardly protruding annular edge for removably securing the clamping ring together with the membrane to the sensing unit by virtue of the lip resiliently snapping into a peripheral groove of the sensing unit, the lip defining the periphery of the annular recess; and
    means including an auxiliary retainer element, for temporarily and removably assembling the membrane with the clamping ring prior to assembly with the sensing unit, wherein the auxiliary retainer element includes a retainer ring fitted loosely into the annular recess of the clamping ring, the retainer ring maintaining the outer rim of the membrane within the annular recess.

2. A retainer arrangement for applying a membrane to a physiological sensing unit for the transcutaneous determination of the magnitude of physiological quantities, particularly for measuring the partial pressure of gases in blood or the like, comprising:
    a membrane;
    a clamping ring having a generally central opening and a peripheral annular recess receiving the rim of the membrane so that the membrane spans the opening;
    the clamping ring having a lip in the form of an inwardly protruding annular edge for removably securing the clamping ring together with the membrane to the sensing unit by virtue of the lip resiliently snapping into a peripheral groove of the sensing unit, the lip defining the periphery of the annular recess; and
    means, including an auxiliary retainer element, for temporarily and removably assembling the membrane with the clamping ring prior to assembly with the sensing unit, wherein the auxiliary retainer element includes a film disc whose rim is removably fitted into the annular recess of the clamping ring to maintain the membrane rim within the annular recess.

3. Retainer arrangement according to claim 1 or claim 2, comprising a removable self-adhesive backing film temporarily supporting at least one clamping ring accommodating a membrane by adhesion to the lip of the clamping ring and to the central surface area which is surrounded by the lip.

4. Retainer arrangement according to claim 3, including a plurality of clamping rings, each accomodating one respective membrane, supported by the backing film for ready use by removal from the backing film and assembly with a physiological sensing unit each of the clamping rings including a retainer element fitted loosely into its annular recess to maintain the outer rim of the membrane within the annular recess.

5. The retainer arrangement of claim 1, wherein the clamping ring is slightly inclined outward from its center prior to assembly onto the sensing unit whereby engagement of the groove by the lip results in a pressing stress between the sensing unit and clamping ring.

6. The retainer arrangement of claim 2, wherein the clamping ring is slightly inclined outward from its center prior to assembly onto the sensing unit whereby engagement of the groove by the lip results in a pressing stress between the sensing unit and clamping ring.

7. A preassembly arrangement for applying a replaceable membrane to a physiological sensing unit for the transcutaneous determination of the magnitude of physiological quantities, particularly for measuring the partial pressure of gases in blood comprising:
    a membrane;

a clamping ring having a generally central opening and a peripheral annular recess receiving the rim of the membrane so that the membrane spans the opening;

the clamping ring having a peripheral lip in the form of an inwardly protruding annular edge for removably securing the clamping ring together with the membrane to the sensing unit by virtue of the lip resiliently snapping into a peripheral groove of the sensing unit, a retaining element fit into the annular recess of the clamping ring to maintain the membrane therewithin;

a sheet of backing material;

a disc of stiff material having a rim removably fitted into the annular recess of the clamping ring; and a layer of adhesive affixing the disc to the sheet.

8. The pre-assembly arrangement of claim 7, wherein the lip defines the periphery of the recess and the disc is removably retained within the recess by the lip.

9. The pre-assembly arrangement of claim 7, wherein the disc fits snuggly within the recess.

10. The pre-assembly arrangement of claim 9 wherein the lip defines the periphery of the recess and the disc is removably retained within the recess by the lip.

11. The pre-assembly arrangement of claim 7, wherein the disc is formed from stiff paper.

12. The pre-assembly arrangement of claim 7, wherein the disc is round.

13. The pre-assembly arrangement of claim 7, wherein the clamping ring is slightly inclined outward from its center prior to assembly onto the sensing unit whereby engagement of the groove by the lip results in a pressing stress between the sensing unit and clamping ring.

* * * * *